(12) United States Patent
Kariniemi (10) Patent No.: US 8,940,015 B2
(45) Date of Patent: Jan. 27, 2015

(54) ASYMMETRICAL MEDICAL DEVICES FOR TREATING A TARGET SITE AND ASSOCIATED METHOD

(75) Inventor: Ryan Kariniemi, Cokato, MN (US)

(73) Assignee: AGA Medical Corporation, Plymouth, MN (US)

( * ) Notice: Subject to any disclaimer, the term of this patent is extended or adjusted under 35 U.S.C. 154(b) by 925 days.

(21) Appl. No.: 12/268,756

(22) Filed: Nov. 11, 2008

(65) Prior Publication Data

US 2010/0121370 A1    May 13, 2010

(51) Int. Cl.
  *A61B 17/08*   (2006.01)
  *A61B 17/00*   (2006.01)
  *A61B 17/12*   (2006.01)
  *A61M 25/00*   (2006.01)

(52) U.S. Cl.
  CPC ....... *A61B 17/0057* (2013.01); *A61B 17/12109* (2013.01); *A61B 17/12113* (2013.01); *A61B 17/12122* (2013.01); *A61B 17/12172* (2013.01); *A61B 17/12022* (2013.01); *A61B 2017/00526* (2013.01); *A61B 2017/00592* (2013.01); *A61B 2017/00606* (2013.01); *A61B 2017/00615* (2013.01); *A61B 2017/00867* (2013.01); *A61M 25/00* (2013.01)
  USPC .......................................... 606/213; 606/151

(58) Field of Classification Search
  USPC ........ 606/151, 200, 213, 152–158; 623/23.72
  See application file for complete search history.

(56) References Cited

U.S. PATENT DOCUMENTS

| | | | |
|---|---|---|---|
| 5,725,552 A * | 3/1998 | Kotula et al. | 606/213 |
| 6,468,303 B1 | 10/2002 | Amplatz et al. | |
| 6,932,837 B2 | 8/2005 | Amplatz et al. | |
| 6,964,674 B1 * | 11/2005 | Matsuura et al. | 606/213 |
| 2003/0181988 A1 * | 9/2003 | Rousseau | 623/23.72 |
| 2004/0044364 A1 * | 3/2004 | DeVries et al. | 606/213 |
| 2006/0224183 A1 | 10/2006 | Freudenthal | |
| 2006/0253184 A1 | 11/2006 | Amplatz | |
| 2007/0073337 A1 * | 3/2007 | Abbott et al. | 606/213 |
| 2007/0118207 A1 | 5/2007 | Amplatz et al. | |
| 2007/0129755 A1 | 6/2007 | Abbott et al. | |
| 2007/0225760 A1 | 9/2007 | Moszner et al. | |
| 2007/0265656 A1 | 11/2007 | Amplatz et al. | |
| 2008/0071301 A1 | 3/2008 | Matsuura et al. | |
| 2011/0046662 A1 | 2/2011 | Moszner et al. | |

FOREIGN PATENT DOCUMENTS

| | | |
|---|---|---|
| DE | 10 2006 013770 A1 | 9/2007 |
| WO | WO-2004/064671 A2 | 8/2004 |
| WO | WO-2008/040555 A2 | 4/2008 |

OTHER PUBLICATIONS

U.S. Appl. No. 11/966,397, filed Dec. 28, 2007, Amplatz et al.
European Search Report for Application No. EP13163815, dated Jul. 17 2013.

* cited by examiner

*Primary Examiner* — Gregory Anderson
*Assistant Examiner* — Alexander Orkin
(74) *Attorney, Agent, or Firm* — Armstrong Teasdale LLP (57) ABSTRACT

Embodiments of the present invention provide medical devices and methods for treating a target site within the body, such as for treating vascular abnormalities. For example, one embodiment provides medical device including a first tubular member that includes a first portion, a second portion, and a central portion disposed between the first portion and the second portion. Each of the first and second portions have a radius that is larger than that of the central portion, and the second portion has a preset, relaxed configuration in which a portion of the second portion has a partial discoid shape defined by an inversion of a portion of a discoid into itself.

24 Claims, 8 Drawing Sheets

ASYMMETRICAL MEDICAL DEVICES FOR TREATING A TARGET SITE AND ASSOCIATED METHOD

BACKGROUND OF THE INVENTION

1) Field of the Invention

The present invention relates to medical devices and, in particular, to asymmetrical devices for treating a target site within the body, such as a vascular abnormality.

2) Description of Related Art

A wide variety of intracardiac prosthetic devices are used in various medical procedures. For example, certain intravascular devices, such as catheters and guide wires, are generally used to deliver fluids or other medical devices to specific locations within the vascular system of a patient, such as a selective coronary artery. Other devices are used in treating specific conditions, such as devices used in removing vascular occlusions or for treating septal defects and the like. For example, devices have been developed for treating abnormalities, such as an Atrial Septal Defect (ASD), a Ventricular Septal Defect (VSD), a Patent Ductus Arteriosus (PDA), a Patent Foramen Ovale (PFO), as well as conditions that result from previous medical procedures such as Para-Valvular Leaks (PVL) following surgical valve repair or replacement.

However, the ability of these devices to treat particular areas of the vasculature or for particular patients may be limited. In particular, conventional devices are typically symmetrical in geometry and material properties, which may be disadvantageous for treating particular target sites. For example, it has been theorized that excessive clamping force in the area of the Bundle of HIS when treating a ventricular septal defect may increase the risk of heart block. In addition, conventional devices that are positioned in the heart may interfere with heart valve function or abrade heart tissue. Moreover, symmetrical devices may provide inadequate fixation or positioning within particular sites to be treated and may limit the effectiveness of the device.

Accordingly, it would be advantageous to provide a reliable medical device that is both easy to deploy through a catheter and that can be accurately placed in a target site. It would also be desirable to provide a low-profile recoverable device for deployment in a target site. Moreover, there is also a need for a medical device that may be effectively fixated within a target site while reducing the incidence of complications resulting from being fixated therein.

BRIEF SUMMARY OF THE INVENTION

Embodiments of the present invention may provide improvements over the prior art by, among other things, providing medical devices and methods for treating a target site within the body. For example, the medical device may be an occluder for treating various target sites with the vasculature. According to one embodiment of the present invention, the medical device comprises at least one layer of fabric, such as a plurality of braided strands. The fabric layer may be a shape memory alloy and be configured to facilitate thrombosis.

One embodiment provides a medical device comprising a first tubular member that includes a first portion, a second portion, and a central portion disposed between the first portion and the second portion. The first and second portions have radii that are larger than that of the central portion, and the second portion has a preset, relaxed configuration in which a portion of the second portion has a partial discoid shape defined by an inversion of a portion of a discoid into itself. For example, the first portion may be disk shaped, while the second portion may be half-disk shaped. In addition, the first and second portions may include different stiffness. Similarly, the first portion may have a preset, relaxed configuration in which a portion of the first portion has a partial discoid shape defined by an inversion of a portion of a discoid into itself. According to one aspect, the first tubular member is configured to be positioned within a septum, and the first and second portions are configured to provide an asymmetrical clamping force on the septum. Moreover, the first tubular member may further include a third portion and a fourth portion each having a larger radius than that of said central portion. The third and fourth portions may have a partial or full discoid shape. The central portion may extend at an oblique angle with respect to said first and second portions.

According to additional aspects of the medical device, the medical device may further include a second tubular member that is coupled to the first tubular member and includes a first portion, a second portion, and a central portion disposed between the first and second portions of the second tubular member. The first and second portions of the second tubular member have radii larger than that of the central portion of the second tubular portion. The first and second tubular members may be coupled such that at least a portion of the second portion of the first tubular member is received by the first or second portion of the second tubular member. In addition, the second portion of the second tubular member may have a preset, relaxed configuration in which a portion of the second portion has a partial discoid shape defined by an inversion of a portion of a discoid into itself. The first and second tubular members may be coupled such that the partial discoid shape portions of the second portions of the first and second tubular members are adjacently disposed and cooperate to define a substantially disk-shaped structure. The first and second tubular members may be coupled such that at least a portion of the partial disk shape portion of the second portion of the first tubular member receives at least a portion of the second portion of the second tubular member. The first and second tubular members may be at least partially formed of respective materials having differing stiffness, such as layers of fabric having differing densities or strand diameters.

According to an additional embodiment, a medical device is provided that includes a central portion and a first portion coupled to the central portion and having a radius larger than that of the central portion. The first portion includes at least one discoid member and at least one partial discoid member having a different stiffness, wherein the partial discoid member being disposed asymmetrically about a circumference of the discoid member. The medical device may also include a second portion coupled to the central portion and having a radius larger than the central portion, wherein the central portion is disposed between the first and second portions. The discoid member may be disk shaped and have a circumference, and the partial discoid member may be disposed partially about the circumference of the discoid member.

A further embodiment of the present invention is directed to a medical device including a central portion having a central axis and opposing first and second portions coupled by the central portion and having respective radii larger than that of the central portion. The first portion has a preset, relaxed configuration in which the first portion is disposed radially to one side of the central axis and the second portion has a preset, relaxed configuration in which the second portion is disposed radially to both the same side and an opposite side of the central axis as the first portion. The first and second portions may cooperate to define at least one disk shape or at least one disk shape and at least one half-disk shape.

Yet another embodiment of the present invention is directed to a medical device that comprises a first tubular member that includes opposing first and second portions coupled by a central portion and having respective radii larger than that of the central portion. The central portion has a central axis and the opposing first and second portions are separated by a non-uniform distance along the central axis. The medical device further includes a second tubular member that is coupled to the first tubular member and includes opposing first and second portions that are coupled by a central portion and have respective radii larger than that of the central portion. The central portion of the second tubular member may have a second central axis and the opposing first and second portions of the second tubular member may be separated by a non-uniform distance along the second central axis. The opposing members of the first and second tubular members may be discoid shaped. Moreover, at least a portion of the first opposing portions of the first and second tubular members may be configured to be positioned adjacent to one another, and at least a portion of the second opposing portions of the first and second tubular members may be configured to be positioned adjacent to one another.

Additional embodiments of the present invention are related to methods of fabricating a medical device and delivering a medical device to a target site within the body. For example, a method of fabricating a medical device includes braiding a first tubular member about a mandrel, wherein the first tubular member includes a first portion, a second portion, and a central portion disposed between the first portion and the second portion, and wherein the first and second portions have a radius larger than that of the central portion. The method further includes radially inverting at least a portion of the second portion within itself to define a partial discoid shape and heat setting the first tubular member while the second portion is inverted.

Aspects of the method include braiding a second tubular member about a mandrel, wherein the second tubular member includes a first portion, a second portion, and a central portion disposed between the first portion and the second portion, and wherein the first and second portions have larger radii than that of the central portion. The method may also include positioning the first and second tubular members adjacent to one another and coupling the first and second tubular members together. Furthermore, the method may include positioning at least a portion of the second tubular member within the inverted portion of the first tubular member. The method may include radially inverting at least a portion of the second portion of the second tubular member within itself to define a partial discoid shape and heat setting the second tubular member while the second portion is inverted. The method may also include positioning the inverted portion of the second portion of the second tubular member within the inverted portion of the second portion of the first tubular member.

An exemplary method of delivering a medical device to a target site within the body includes providing a medical device comprising a first tubular member that includes a first portion, a second portion, and a central portion disposed between the first portion and the second portion, wherein the first and second portions have larger radii than that of the central portion, and wherein the second portion has a preset, expanded configuration in which a portion of the second portion has a shape defining a partial discoid. The method also includes constraining the medical device to the reduced shape and positioning the constrained medical device in a catheter. In addition, the method includes delivering the medical device proximate to the target site and deploying the medical device from the catheter such that the medical device assumes the preset, expanded configuration. The method may further include providing a second tubular member coupled to the first tubular member and including a first portion, a second portion, and a central portion disposed between the first and second portions of the second tubular member, wherein the first and second portions of the second tubular member have larger radii than that of the central portion of the second tubular portion. A portion of the second portion may have a shape defining a partial discoid.

BRIEF DESCRIPTION OF THE SEVERAL VIEWS OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a medical device for use in treating a target site within the body, such as occluding various vascular abnormalities, which may include, for example, occluding an Arterial Venous Malformation (AVM), an Atrial Septal Defect (ASD), a Ventricular Septal Defect (VSD), a Patent Ductus Arteriosus (PDA), a Patent Foramen Ovale (PFO), conditions that result from previous medical procedures such as Para-Valvular Leaks (PVL) following surgical valve repair or replacement, and the like. It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a congenital defect, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, a septum, or the like.

As explained in further detail below, a medical device according to one embodiment of the present invention includes an asymmetrical configuration including at least one layer of occlusive material. For instance, the medical device may be asymmetric in its material properties and/or geometry. The asymmetrical configuration may be adaptable for various target sites to thereby facilitate fixation and treatment at the target site, such as for occluding a lumen.

According to one embodiment of the present invention for forming a medical device of the invention, the device includes one or more layers of braided fabric formed of a plurality of wire strands having a predetermined relative orientation with respect to one another. Moreover, the device may comprise a plurality of layers of occluding material such that the device may be a variety of occluding materials capable of at least partially inhibiting blood flow therethrough in order to facilitate the formation of thrombus and epithelialization around the device.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

As used herein, "substantially preclude or impede flow" shall mean, functionally, that blood flow may occur for a short time, e.g., about 3-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the device and if no contrast media flows through the wall of the device after a predetermined period of time as viewed by fluoroscopy, then the position and occlusion of the device is adequate. Moreover, occlusion of the target site could be assessed using various ultrasound echo doppler modalities.

As used herein the term "proximal" shall mean closest to the operator (less into the body) and "distal" shall mean furthest from the operator (further into the body). In positioning of the medical device from a downstream access point, distal is more upstream and proximal is more downstream.

According to one embodiment, the occlusive material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. It is also understood that the device may comprise various materials and combinations of materials other than Nitinol that have elastic properties, such as spring stainless steel, alloys such as Elgiloy®, Hastelloy®, CoCrNi alloys (e.g., trade name Phynox), MP35N®, CoCrMo alloys, or polymeric materials. Depending on the individual material selected, the wire strand diameter, number of wire strands and pitch may be altered to achieve the desired properties of the device. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One may solder, braze, weld, coat, glue, clamp, tie or otherwise affix the ends of the desired length together. According to one embodiment, each layer of the device may comprise 36-288 wire strands ranging in diameter from about 0.0005 to 0.010 in. formed of a shape memory alloy, such as Nitinol, that are braided so as to define fenestrations with an area of about 0.00015 to 0.015 sq. in., which are sufficiently small so as to slow the blood flow through the wall of the device and to facilitate thrombus formation thereon. For example, one embodiment includes a braid having 144 Nitinol strands with a strand diameter of about 0.0025 to 0.003 in. Inner and outer braided layers may have pitch angles that are about equal to obtain desirable collapse and expansion characteristics, such as maintaining a uniform overall length.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element may be selected to deform the fabric into substantially the shape of the desired medical device when unconstrained. Once the molding element is assembled with the metal fabric generally conforming to a molding surface of that element, the fabric may be subjected to a heat treatment while it remains in contact with that molding surface. After the heat treatment, the fabric is removed from contact with the molding element and will substantially retain its shape in a deformed state. As explained in further detail below in conjunction with the illustrated embodiments, different configurations of devices may be formed and heat set for various locations within the body.

Those skilled in the art will appreciate that in order to speed up the occlusion of the vessel device, the device may be coated with a suitable thrombogenic agent, filled with a polyester fiber, or braided with an increased number of wire strands. The interwoven fiber may attach to a clot to retain the clot firmly within the device as it forms the occlusion.

The device may include a plurality of planes of occlusion. A plane of occlusion may be any surface, whether flat or irregular in shape, that may be oriented at least partially transverse to the flow of blood so as to facilitate the formation of thrombus. At least one plane of occlusion may include one or more layers of occlusive material, such as a layer of fabric and/or a layer of polyester fiber, two layers of metal, or two layers of polyester. Thus, by modifying the configuration of the device, the number of planes of occlusion may be modified, and by changing the number of layers of occlusive material, the rate at which the device occludes the vascular abnormality may also be modified.

Once a device having a preselected shape has been formed, the device may be used to treat a physiological condition of a patient. A medical device suitable for treating the condition, which may be substantially in accordance with one of the embodiments outlined below, is selected. Once the appropriate medical device is selected, a catheter or other suitable delivery device may be positioned within a channel in a patient's body to place the distal end of the delivery device adjacent the desired treatment site, such as immediately adjacent (or even within) the shunt of an abnormal opening in the patient's organ for example.

The delivery device (not shown) can take any suitable shape, such as an elongate flexible polymer or metal shaft, cable, hypotube or metal braided polymer tube configured to constrain the medical device. The device may include no clamps or one or more clamps for engagement with the delivery device. For example, the delivery device may include a threaded distal end for engagement with a threaded bore formed in the clamp of the medical device. The delivery device can be used to urge the medical device through the lumen of a catheter/sheath for deployment in a channel of a patient's body. When the medical device is deployed out the distal end of the catheter, the delivery device still will retain it. Once the medical device is properly positioned within the shunt of the abnormal opening, the shaft of the delivery device can be rotated about its axis to unscrew the medical device from the delivery device. As also explained in further detail below, the specific delivery method will depend on the particular device to be deployed within the body.

In one embodiment the medical device, the delivery catheter, and catheter/sheath accommodate a coaxial guidewire that slideably passes through the device, end clamp(s) and delivery catheter central lumen, and therefore helps guide the delivery device and outer catheter/sheath to the desired location. The guidewire may be delivered independently through the vasculature and across the targeted treatment location or may be extended partially distal to the distal end of the delivery device and catheter/sheath and advanced with the delivery device and catheter/sheath while the guidewire is manipulated to guide the occluder to the desired location. In another embodiment, the catheter/sheath is steerable to assist in placement of the delivery device and occluder. For further discussion regarding a delivery device and methods that may be used to deploy a device according to various aspects of the present invention, see U.S. patent application Ser. No. 11/966,397, which is hereby incorporated in its entirety by reference.

In another embodiment, the device does not have end clamps and the delivery device engages the wire ends at the proximal end of the device between a sleeve and a bead. The sleeve may be connected to a hollow shaft, and the bead may be connected to a cable or wire that passes through the shaft. Relative movement between the bead and the sleeve either engages or releases the braid wire ends at the proximal end of the device. When the wire ends are engaged the delivery device can control the advancement of the device through the delivery catheter. For a further exemplary discussion regarding this delivery device as well as an over the wire version of it, see U.S. Patent Appl. Publ. No. 2007/0118207 to Amplatz et. al., which is hereby incorporated in its entirety by reference.

By keeping the medical device attached to the delivery device, the operator can retract the device for repositioning relative to the abnormal opening, if it is determined that the device is not properly positioned. A delivery device attached to the medical device may allow the operator to control the manner in which the medical device is deployed out the distal end of the catheter. When the medical device exits the catheter, it will tend to resiliently return to a preset, expanded shape, which is set when the fabric is heat-treated. When the device self expands and springs back into this shape, it may tend to act against the distal end of the catheter effectively urging itself forward beyond the end of the catheter. This spring action could conceivably result in improper positioning of the device if the location of the device within the body is critical, such as where it is being positioned in a shunt between two vessels. Since the delivery device can enable the operator to maintain a hold on the device during deployment, the spring action of the device can be controlled by the operator to ensure proper positioning during deployment.

The medical device can be constrained into its reduced diameter configuration and inserted into the lumen of the catheter. According to one embodiment, the medical device may be constrained to an outer diameter of less than about 11 French for delivery within a catheter. The collapsed configuration of the device may be of any shape suitable for easy passage through the lumen of a catheter and proper deployment out the distal end of the catheter. For example, the device may have a relatively elongated collapsed configuration wherein the device is stretched along its axis. This collapsed configuration can be achieved simply by stretching the device generally along its axis, e.g. by manually grasping the ends of the device and pulling them apart, which will tend to collapse the expanded diameter portions of the device inwardly toward the device's axis. In this regard, these devices are not unlike "Chinese handcuffs", which tend to constrict in diameter under axial tension.

If the device is to be used to permanently occlude a flow passageway in the patient's body, one can simply retract the catheter and remove it from the patient's body. This will leave the medical device deployed in the patient's vascular system so that it may occlude the target site, such as a blood vessel, septal defect, or other channel in the patient's body. In some circumstances, the medical device may be attached to a delivery system in such a manner as to secure the device to the end of the delivery device. Before removing the catheter in such a system, it may be necessary to detach the medical device from the delivery device before removing the catheter and the delivery device.

Although the device will tend to resiliently return to its initial expanded configuration, i.e., its shape prior to being collapsed for passage through the catheter, it should be understood that it might not always return entirely to that shape. For example, it may be desirable that the device has a maximum outer diameter in its expanded configuration at least as large as and preferably larger than, the inner diameter of the opening in which it is to be deployed. For instance, the outer diameter of the device may be about 10-30% larger than the inner diameter of the opening. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat and retain the device therein.

When the device is deployed in a patient, thrombi will tend to collect on the surface of the strands. By having a greater strand density and smaller flow passages between strands as afforded by the multiple layer construction of the present invention, the total surface area of the strands and flow resistance will be increased, increasing the thrombotic activity of the device and permitting it to relatively rapidly occlude the vessel in which it is deployed. The device may be delivered and properly placed using two dimensional ICE, MRI, transesophageal echocardiography, angiography, and/or Doppler color flow mapping. With the advent of two dimensional ICE, MRI, trans-esophageal echocardiography, bi-plane angiography, and Doppler color flow mapping, the approximate anatomy of the defect can be visualized. The device that is employed will be based on the approximate size of the vessel or abnormality in which the device is to be placed.

In use, the medical devices would be delivered at a diameter that is smaller than its heat set diameter. Typically, the medical devices would be constrained, such as by axially elongating the medical devices to a smaller diameter and positioning the distal end of the fabric wires within a delivery catheter for delivery to a target site. For those medical devices having a clamp member at its proximal end, the clamp member may be engaged by a delivery device, such as by threadable engagement, and inserted within a delivery catheter. When the medical device is deployed out the distal end of the catheter, the device will still be retained by the delivery device. Once the proper position of the medical device in the vessel, body organ, or the like is confirmed, the shaft of the delivery device may be rotated about its axis to unscrew the clamp member from the threaded end of the delivery device. Of course, the threaded connection could be at either end of the medical device depending on the anatomical situation and the desired or available means of access to the treatment site.

By keeping the medical device attached to the delivery system, the operator may still retract the medical device back into the delivery catheter for repositioning if it is determined that the medical device is not properly positioned in the first attempt. In instances where the medical device is improperly deployed on a first try, the device may be recovered by pulling the delivery device proximally, thereby retracting the medical device back into the delivery catheter prior to a second attempt at positioning the medical device relative to the vessel, body organ, or the like. The threaded attachment may also allow the operator to control the manner in which the medical device is deployed out of the distal end of the delivery catheter. As explained below, when the medical device exits the delivery catheter it will tend to resiliently return to an expanded shape which was set when the fabric was heat treated. When the device springs back into this shape, it may tend to act against the distal end of the catheter, effectively urging itself forward beyond the end of the catheter. This spring action could conceivably result in improper positioning of the device. Since the threaded clamp member can enable the operator to maintain a hold on the device during deployment, the spring action of the device can be controlled and the operator can control the deployment to ensure proper positioning.

The delivery device may be releasably attached to the medical device prior to insertion into the delivery catheter. The delivery catheter, medical device, and delivery device, would be introduced into the patient together, through an introducer sheath and placed using the Seldinger technique to gain vascular access such as through the femoral artery. The medical device would then be guided through the vascular system until a distal end of the delivery catheter is proximate to a target site to be treated, such as within a lumen. With the medical device and the delivery device held stationary, the delivery catheter is withdrawn in the proximal direction to partially eject the medical device from the distal end of the delivery catheter until a distal portion of the medical device then self-expands to engage the lumen. The natural tendency of the medical device is to return to the expanded heat set configuration once released from the catheter, although some intervention by the physician may be necessary in order for the medical device to return to the heat set configuration and be fully deployed. When the medical device is fully deployed from the delivery catheter, the clamp member may be actuated to release the proximal end of the medical device. For further exemplary details regarding a delivery catheter, a delivery device, clamp member, and over-the-wire delivery, and methods of using the same, Applicants hereby incorporate U.S. Patent Appl. Publ. No. 2006/0253184, filed May 4, 2005 and U.S. Patent Appl. Publ. No. 2007/0118207A1, filed Jan. 17, 2007, herein in their entirety.

In an alternative technique for delivering a medical device, a guide wire may be inserted through an introducer sheath and advanced to the treatment site. A delivery catheter may then be introduced over the guide wire and tracked to the treatment site. The medical device attached proximally to the delivery device may then be introduced over the guide wire or alternatively the guide wire removed. The distal end of the device may be loaded into the funnel introducer and fed into the proximal lumen of the delivery catheter and advanced using the delivery device to place the distal end of the device near the distal end of the delivery catheter. The medical device may then be deployed as previously described above.

Referring now to the drawings, a discussion of the embodiments of various medical devices of the present invention will next be presented. For instance, the medical devices or variations there of could be used for treating an Arterial Venous Malformation (AVM), an Atrial Septal Defect (ASD), a Ventricular Septal Defect (VSD), a Patent Ductus Arteriosus (PDA), a Patent Foramen Ovale (PFO), conditions that result from previous medical procedures such as Para-Valvular Leaks (PVL) following surgical valve repair or replacement, and the like.

Figure 1:
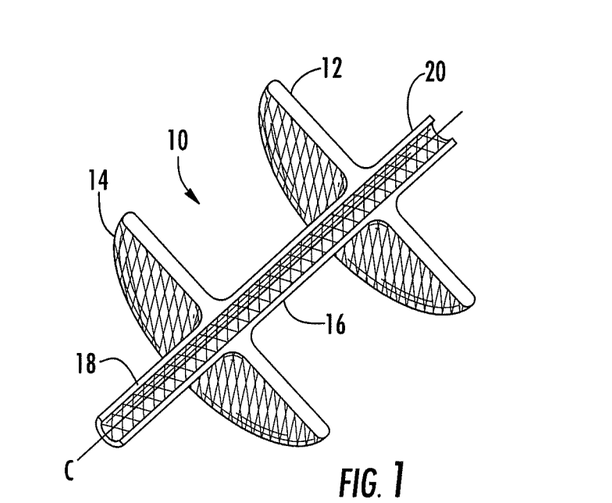
FIG. 1 illustrates a perspective view of an occlusion device according to one embodiment of the present invention.

For example, FIG. 1 illustrates one embodiment of the present invention wherein the medical device 10 is an occluder. The device 10 includes a pair of partial discoid portions 12, 14 axially spaced apart by a central portion 16 along a central axis C. The device 10 may also include proximal 18 and distal 20 portions extending axially along the central axis C. Each discoid portion 12, 14 includes a radially concave surface that may be formed, for instance, by inverting a portion of the discoid within itself. Thus, by being inverted within itself, the device 10 may include a plurality of adjacent or overlying layers (e.g., a single layer device may be inverted to form a double layer device). For example, each discoid portion 12, 14 may initially be disk shaped and then inverted within itself to form a half-disk shape. Furthermore, the central portion 16 and end portions 18, 20 may include radially concave surfaces and be at least partially inverted within itself such that the device 10 may include a radially concave surface between its proximal and distal ends. The medical device 10 may be formed from a tubular structure and shaped into the desired configuration and heat set as described above. For instance, a portion of the medical device 10 may be compressed in order to form the partial discoid portions 12, 14 and then heat set. Moreover, the tubular structure may include one or more layers of material and inverted to double the wall thickness when radially inverted.

Figure 2:
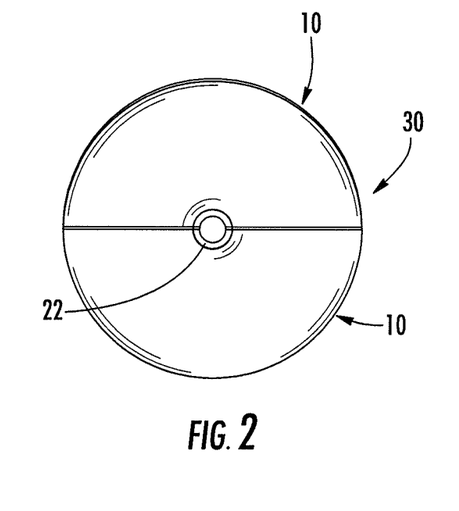
FIG. 2 illustrates an end view of an occlusion device according to one embodiment of the present invention.
Figure 3:
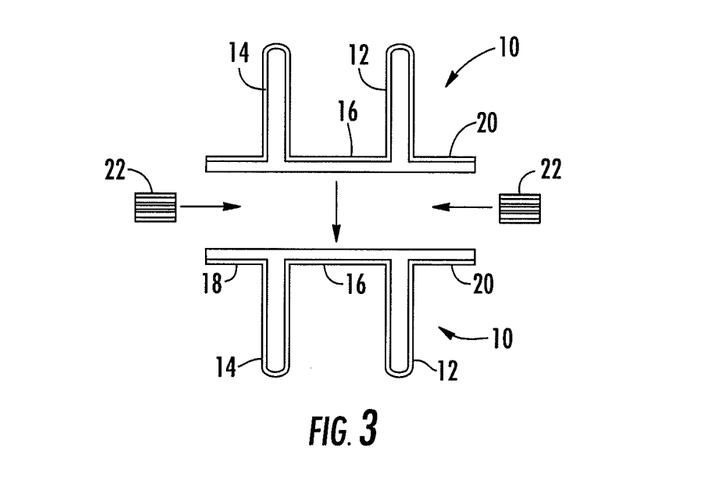
FIG. 3 illustrates an exploded cross-sectional view of the occlusion device shown in FIG. 2.
Figure 4:
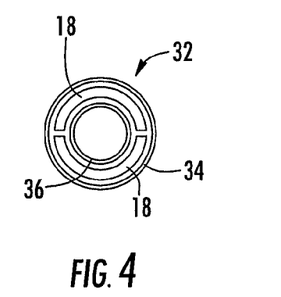
FIG. 4 illustrates a cross-sectional view of a clamp assembly for an occlusion device according to one embodiment of the present invention.

FIGS. 2 and 3 illustrate one embodiment where a pair of medical devices 10 is coupled to form an occluder device 30. Thus, the partial discoid portions 12, 14 of respective medical devices may be positioned adjacent to one another to cooperatively define a pair of full discoid portions, such as substantially disk-shaped members. The medical devices 10 may be coupled together by clamping the proximal 18 and distal 20 ends of respective devices with clamps 22 or the like. For instance, FIG. 4 illustrates a clamping assembly 32 that includes outer 34 and inner 36 clamps. In particular, FIG. 4 shows that a respective outer clamp 34 is configured to receive the proximal 18 end (or distal end 20) of each medical device 10, while a respective inner clamp 36 is positioned within the proximal ends. Thus, the proximal 18 or distal ends 20 may be sandwiched between the outer 34 and inner 36 clamps. The medical devices 10 could also or alternatively be coupled together at various locations between the proximal 18 and distal 20 ends, such as by additional clamps or by suturing adjacent portions of the discoid portions 12, 14 and/or central portions 16 together.

Figure 5:
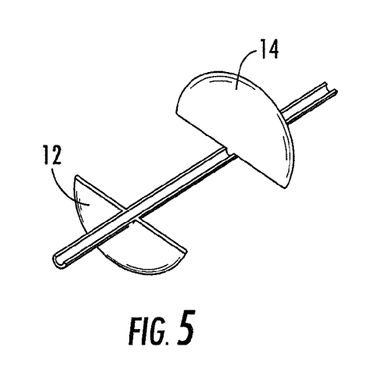
FIG. 5 illustrates a perspective view of an occlusion device according to an additional embodiment of the present invention.

It is understood that the medical devices 10 may have a variety of configurations according to additional embodiments of the present invention. Thus, the term "discoid" is not meant to be limiting, as a discoid may be a disk, a half-disk, or a generally disk or half-disk shaped member having a circular, elliptical, or other non-circular cross section. In addition, the discoid portions 12, 14, central portion 16, and/or proximal 18 and distal ends 20 may be various shapes such as disk, half-disk, cylindrical, semi-circular, or any other desired shape that is capable of having a radially concave surface. FIG. 5 shows an exemplary embodiment where the partial discoid portions 12, 14 are located on opposite sides of the central axis C, with each discoid having a substantially half-disk shape. Moreover, FIG. 6 illustrates another embodiment of a medical device 38 where one partial discoid portion 12 is substantially a half-disk shape and the other discoid portion 14 is substantially a full-disk shape.

Figure 6:
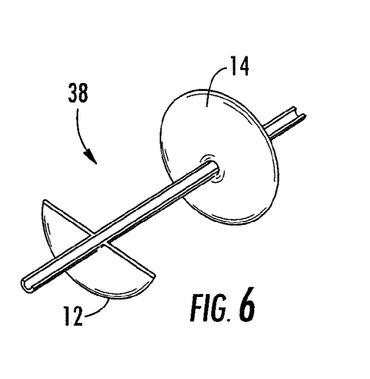
FIG. 6 illustrates a perspective view of an occlusion device according to an additional embodiment of the present invention.
Figure 7:
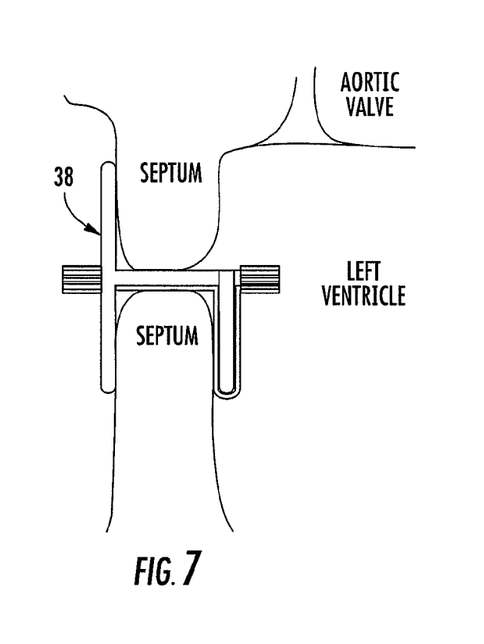
FIG. 7 illustrates a cross-sectional view of the occlusion device shown in FIG. 6 positioned within an opening in the ventricular septum according to an embodiment of the present invention.

The particular configuration shown in FIG. 6 may be advantageous to treat particular target sites, such as a ventricular septum, as shown in FIG. 7. Thus, the central portion 16 may extend through the septum, and the discoid portions 12, 14 may be configured to overlie the opening and the septum. The devices may be heat set such that the discoid portions 12, 14 are biased towards one another when released from the constrained configuration to retain the device in the septum. In addition, the partial discoid portion 12 is positioned opposite the mitral valve, which may reduce the incidence of heart block or interference with the mitral valve.

Furthermore, the medical devices 10 may include different properties in order to apply an asymmetric clamping force. For example, the occluder device 30 shown in FIGS. 2 and 3 may include medical devices 10 having different stiffness. The medical devices 10 could include a different number of braided strands, different strand diameters, or different materials in order to vary the stiffness and, thus, the clamping force. In other words, an occluder device 30 shown in FIG. 3 having an upper medical device 10 made of a softer material and a lower medical device made of a stiffer material could exhibit an asymmetric clamping force, with the lower medical device providing a greater clamping force. The clamping force may also be varied by radially inverting a portion of the medical device within itself to increase the stiffness with respect to portions that are not inverted. For instance, the partial discoid portion 12 of the medical device 10 shown in FIGS. 6 and 7 would be stiffer than the full discoid portion 14. Providing medical devices having different physical properties may be advantageous to treat particular target sites, such as a ventricular septum. In particular, the softer upper half may be located in the region of the aortic valve and around the sinoatrial node which may lower the risk of heart block due to excessive clamping force in the area of the Bundle of HIS. In addition, providing a softer material in select regions of the heart may reduce abrasion of heart tissue while ensuring retention of the device.

Figure 8:
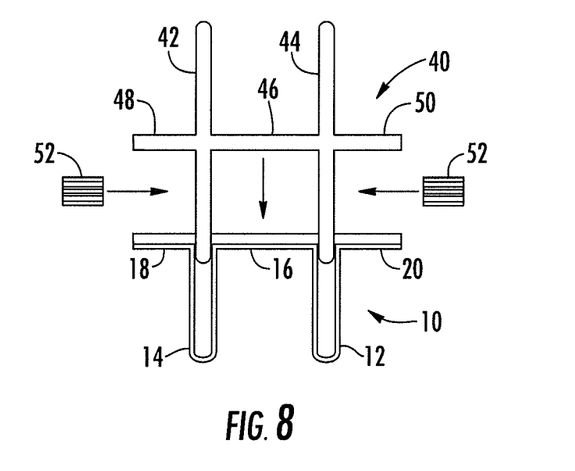
FIG. 8 depicts an exploded cross-sectional view of an occlusion device according to one embodiment of the present invention.
Figure 9:
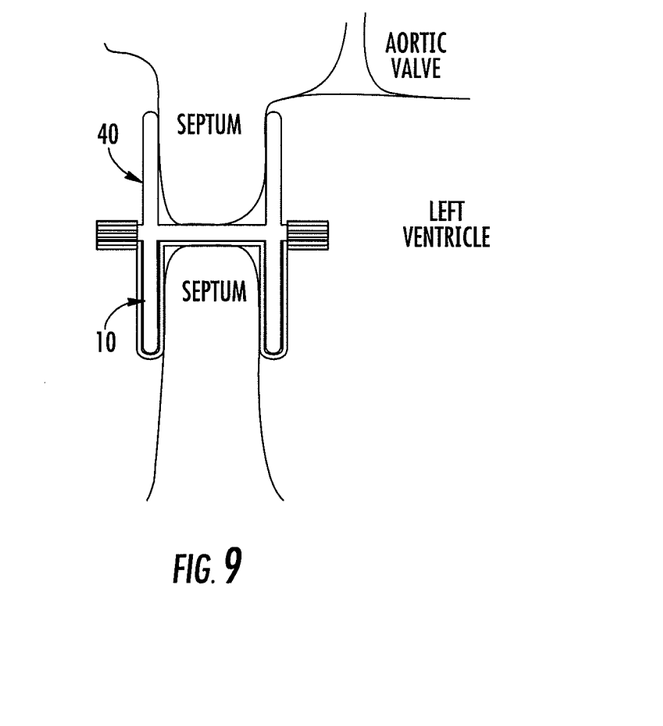
FIG. 9 illustrates a cross-sectional view of the occlusion device shown in FIG. 8 positioned within an opening in the ventricular septum according to an embodiment of the present invention.
Figure 10:
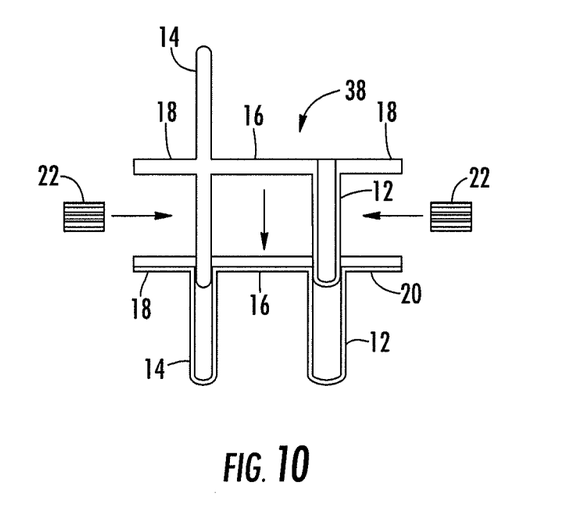
FIG. 10 depicts an exploded cross-sectional view of an occlusion device according to one embodiment of the present invention.

Moreover, it is understood that one or more medical devices 10 may have various configurations and coupled to one another using a variety of techniques. For example, FIG. 8 shows that the medical device 10 may be configured to receive a second medical device 40. In particular, FIG. 8 shows that each partial discoid portion 12, 14 includes a radially concave surface that is configured to receive a portion of respective full discoid portions 42, 44 such as substantially disk-shaped portions. Also, the central portion 16 and proximal 18 and distal 20 ends may also include a radially concave surface that is configured to receive the central portion 46 and proximal 48 and distal 50 ends of the medical device 40. The proximal 18, 48 and distal 20, 50 ends of each medical device 10, 40 may be coupled together with end clamps 52. Thus, when the medical devices 10, 40 are coupled together the wall thickness is increased in each of the overlying areas, which may be advantageous for treating various target sites where more clamping force is needed in one area and greater flexibility is needed in another area. For instance, FIG. 9 shows the coupled medical devices 10, 40 positioned within a ventricular septum.

Figure 11:
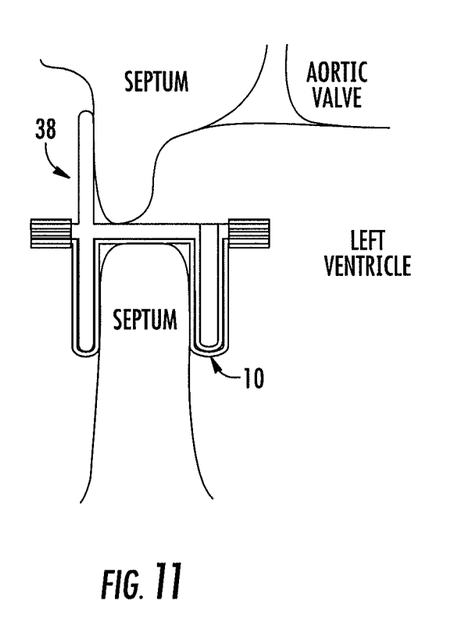
FIG. 11 illustrates a cross-sectional view of the occlusion device shown in FIG. 10 positioned within an opening in the ventricular septum according to an embodiment of the present invention.

FIG. 11 illustrates an additional embodiment where the medical device 10 shown in FIG. 1 is configured to receive a portion of the medical device 38 shown in FIG. 6. Thus, the partial discoid portion 12 of the device 10 is configured to receive the partial discoid portion 12 of the device 38 to cooperatively form substantially a half-disk shape, while the partial discoid portion 14 of the device 10 is configured to receive the full discoid portion of the device 38 to cooperatively form substantially a disk shape. FIG. 11 shows the coupled devices 10, 38 positioned within a ventricular septum.

Figure 12:
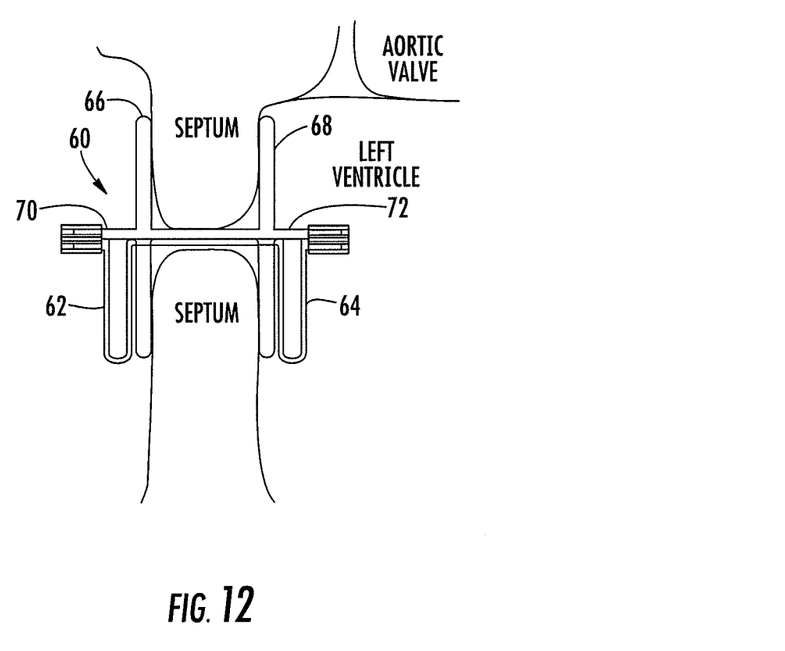
FIG. 12 illustrates a cross-sectional view of an occlusion device positioned within an opening in the ventricular septum according to one embodiment of the present invention.

Moreover, although a pair of discoid portions is shown in each of the aforementioned embodiments, the medical device may include one or more partial or full discoid portions. For example, the medical device 10 could include a partial discoid portion 12 that is positioned adjacent to a second partial discoid portion 14 on an opposite side of the central axis C to form a plug. Moreover, FIG. 12 depicts yet another embodiment of a medical device 60 that include a pair of partial discoid portions 62, 64 and a pair of full discoid portions 66, 68. The partial discoid portions 62, 64 are positioned proximate to the proximal 70 and distal 72 ends. The partial discoid portions 62, 64 may be configured to apply an inward force on the full discoid portions 66, 68 and the walls of the target site being treated, such as the septum as shown in FIG. 12. Thus, although the partial and full discoid portions are shown spaced apart in FIG. 12, the partial discoid portions may overlie respective full discoid portions when deployed at the target site and thereby apply an asymmetric clamping force on the septum.

Figure 13:
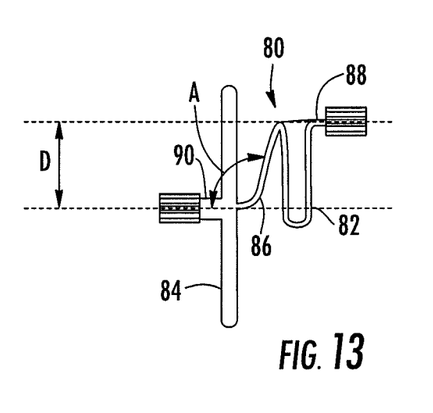
FIG. 13 is a cross-sectional view of an occlusion device according to one embodiment of the present invention.
Figure 14:
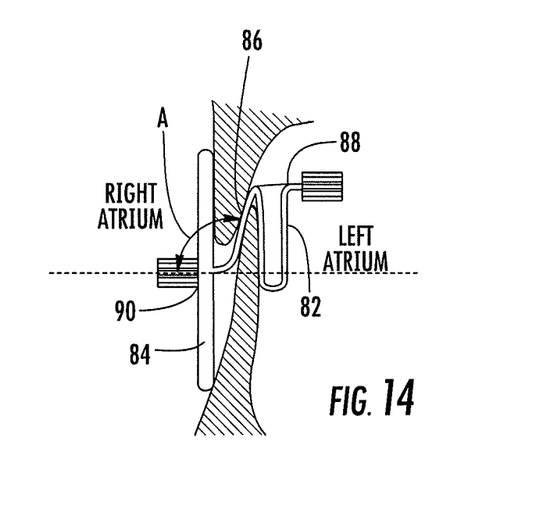
FIG. 14 illustrates the occlusion device of FIG. 13 positioned within a patent foramen ovale.

FIGS. 13 and 14 illustrate an additional embodiment of a medical device 80 that includes a partial discoid portion 82 (e.g., a half-disk shape) and a full discoid portion 84 (e.g., a disk shape) and a central portion 86 extending therebetween. The central portion 86 is oriented at an oblique angle A such that the proximal 90 and distal 88 ends are axially offset from one another by a distance D. The angle A (e.g., between 0 and 90 degrees) and distance D may be varied for treating various target sites. Moreover, although partial 82 and full 84 discoid portions are shown, it is understood that the medical device may be modified depending on the target site being treated. For instance, the device 80 may include a pair of partial discoid portions or a pair of full discoid portions.

According to one embodiment, FIG. 14 shows that the medical device 80 may be used to treat a PFO. In particular, the partial discoid portion 82 may be positioned in the left atrium, the central portion 86 may pass through the PFO tunnel, and the full discoid portion 84 may be positioned in the right atrium. The partial 82 and full 84 discoid portions may be configured to overlie the opening of the PFO tunnel and lie adjacent to the atrium walls, while the central portion 86 may be configured to apply a clamping force that biases the discoid portions towards one another. In this regard, the medical device 80 may be heat set in the configuration shown in FIG. 13, wherein FIG. 13 shows that the central portion 86 extends at a smaller oblique angle A than that shown in FIG. 14. Thus, when the medical device 80 is released from its constrained configuration, the device resiliently returns to its heat set position such that the central portion 86 will tend to bias in a counterclockwise direction which clamps the partial 82 discoid portion against the wall of the left atrium.

Figures 15, 16:
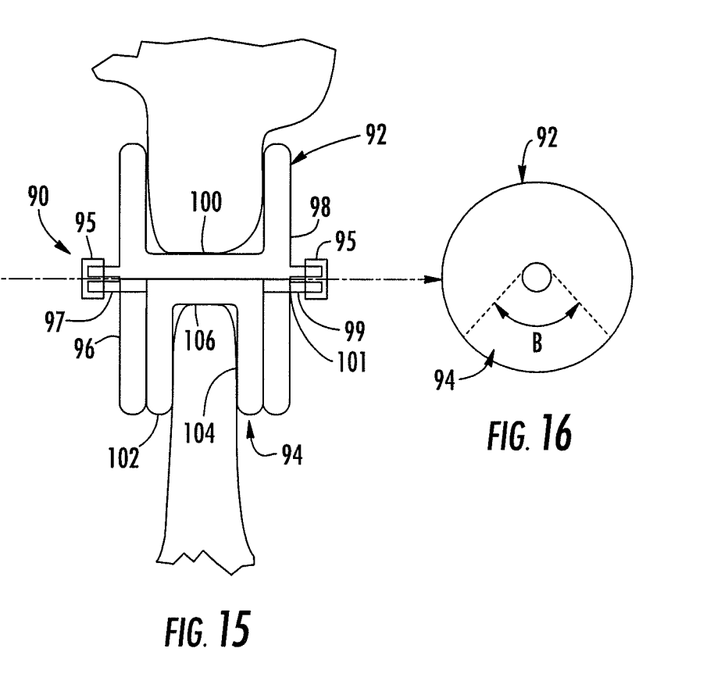
FIG. 15 illustrates a cross-sectional view of an occlusion device positioned within a septum according to one embodiment of the present invention.
FIG. 16 illustrates an end view of the occlusion device shown in FIG. 15 according to one embodiment of the present invention.
Figure 17:
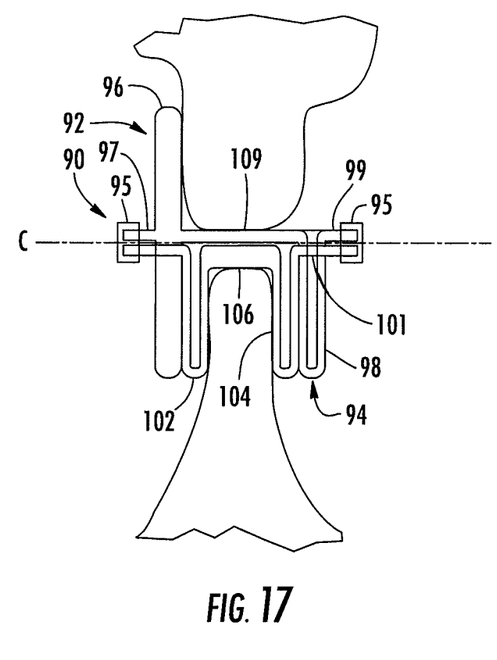
FIG. 17 illustrates a cross-sectional view of an occlusion device positioned within a septum according to an additional embodiment of the present invention.

Additional embodiments of the present invention provide medical devices comprising materials having different physical and/or geometrical characteristics. For instance, the medical device may include multiple layers, may have different stiffness, or different portions of the medical device may have different stiffness. FIGS. 15-17 illustrate exemplary embodiments of medical devices having materials of different material properties. In particular, FIG. 15 shows a medical device 90 that includes an upper half 92 comprising a softer material than a lower half 94. The upper half 92 may be made softer by using different materials, strand diameters, braid densities, number of strands, pick count, or any other technique that would provide greater stiffness to the lower half 94 with respect to the upper half. Thus, the lower half 94 may be configured to apply a greater clamping force than the upper half 92.

The upper 92 and lower 94 halves may be formed from respective tubular members and heat set into a desired configuration. For instance, the upper half 92 may include a pair of full discoid portions 96, 98 and a central portion 100 extending therebetween, while the lower half 94 may include a pair of partial discoid portions 102, 104 and a central portion 106 extending therebetween. Thus, the full discoid portions 96, 98 may be disposed radially on both sides of the central axis C, while the partial discoid portions 100, 102 may be disposed on only one side of the central axis C. The upper half 92 is configured to overlie, and lie adjacent to, at least a portion of the lower half 94.

Moreover, the proximal 97 and distal 99 ends of the device 90 would be secured with respective end clamps 95. In particular, the proximal 97 and distal 99 ends of the upper 92 and lower 94 halves would be secured with respective end clamps 95. In addition, the discoid portions 96, 98 may have openings 101 proximate to each of the proximal 97 and distal 99 ends that are configured to receive the respective ends of the partial discoid portions 102, 104 so that the proximal and distal ends of the upper and lower halves can be secured in the end clamp. The openings 101 could be formed by displacing the braid of the discoid portions 102, 104, heat setting the discoid portions with an opening, or other suitable technique.

Furthermore, FIG. 16 shows an end view of the medical device 90, wherein it is shown that the upper half 92 and lower half 94 are disposed radially asymmetrically about the central axis C with respect to one another. Namely, the upper half 92 is disposed about the entire circumference of the central axis C, while the lower half 94 is disposed only partially about the central axis C at an angle B. FIG. 16 also illustrates that the radii of the upper 92 and lower 94 halves may be substantially similar. However, it is understood that the configuration of the upper 92 and lower 94 halves may be modified for treating various target sites and patients. For example, the radii of the upper 92 and lower 94 halves may be unequal (e.g., the radius of the upper half could be larger), and the lower half may be radially disposed at a variety of angles B (e.g., 180 degrees or less). The braid angle may be different between the upper 92 and lower 94 halves to enable the axially elongated collapsed length of the upper and lower halves to be equal for delivery through a catheter.

According to one particular embodiment, the medical device 90 is employed to treat a Perimembranous Ventricular Septal Defect (PMVSD). In particular, FIG. 15 shows the medical device 90 deployed within a PMVSD. The central portions 100, 106 of the upper 92 and lower 94 halves are positioned through the septum tunnel, while the full discoid portions 96, 98 are configured to overlie the openings of the septum tunnel and lie adjacent to the walls of the septum. The partial discoid portions 102, 104 are also configured to lie adjacent to the walls of the septum on one side of the central axis. The full discoid portions 96, 98 are heat set such that they are biased towards one another and apply a clamping force on the partial discoid portions 102, 104 and the walls of the septum when released from the constrained configuration. Similarly, the partial discoid portions 102, 104 are configured to bias towards one another when released to apply a clamping force on the walls of the septum. The configuration of the softer upper half 92 and stiffer lower half 94 may facilitate in centering the medical device 90 in the tunnel, lowering the risk of heart block due to excessive clamping force, and reducing interference with the aortic valve or abrading the top surface of the left atrium.

Figure 18:
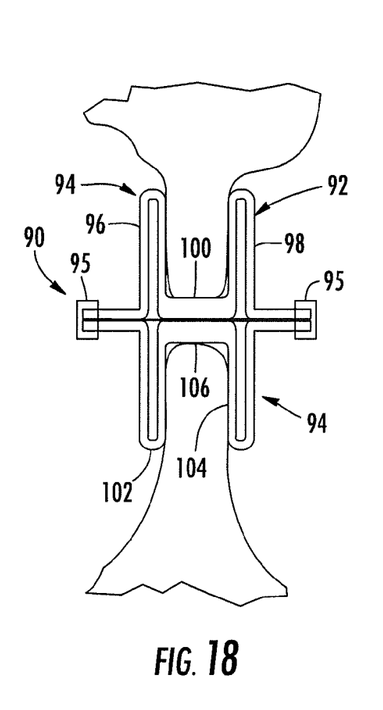
FIG. 18 illustrates a cross-sectional view of an occlusion device positioned within a septum according to one embodiment of the present invention.

It is understood that the medical device 90 may be modified for treating a variety of target sites and patients. For instance, FIG. 17 shows that the upper half 92 may include a full discoid 96 portion and a partial discoid portion 98, while the lower half 94 may include partial discoid portions 102, 104. FIG. 17 illustrates that the partial discoid portions 98 and 104 may be located on the same side of the central axis C. Moreover, FIG. 18 demonstrates that the upper 92 and lower 92 halves may each include partial discoid portions 96, 98 and 102, 104, respectively. More specifically, the upper half 92 includes partial discoid portions 96, 98 on one side of the central axis C, while the lower half 94 includes partial discoid portions 102, 104 on the opposite side of the central axis C. Thus, the partial discoid portions 96, 98 and 102, 104 may cooperate to form a pair of substantially disk shaped portions, which may be configured to apply a selectively varied clamping force on the upper and lower walls of the septum for treating a PMVSD, as shown in FIG. 18.

Figure 19:
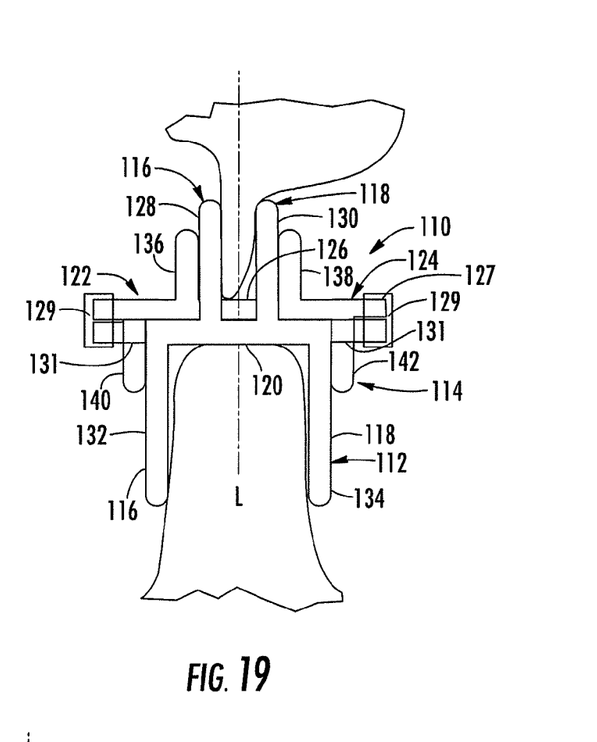
FIG. 19 depicts a cross-sectional view of an occlusion device according to one embodiment of the present invention.
Figure 20:
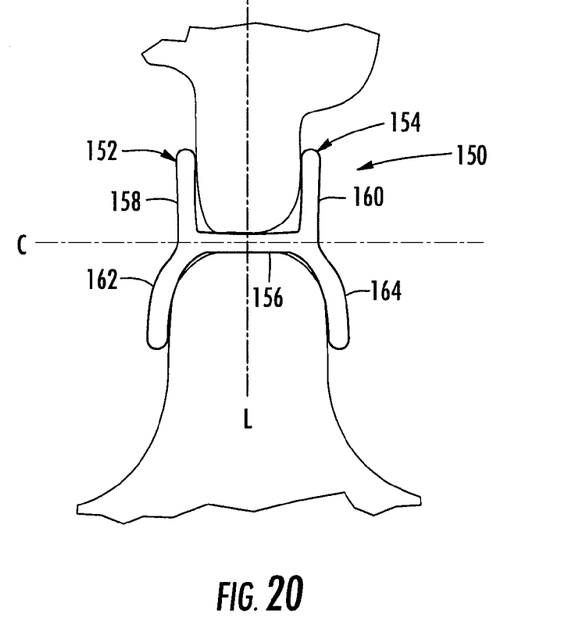
FIG. 20 illustrates a cross-sectional view of an occlusion device positioned within a septum according to an embodiment of the present invention.

FIGS. 19 and 20 depict additional embodiments of medical devices for treating various target sites. For example, FIG. 19 illustrates a medical device 110 having an inner member 112 and an outer member 114. The inner member 112 may be a tubular structure having a pair of full discoid portions 116, 118 coupled by a central portion 120 and, likewise, the outer member 114 may be a tubular structure having a pair of full discoid portions 122, 124 coupled by a central portion 126. The inner 112 and outer 114 members may be separated by a non-uniform distance along axis L. In particular, each discoid portion 116, 118 may include an upper portion 128, 130 that is separated by a distance measured along central axis C that is smaller than a distance separating a lower portion 132, 134 of each discoid portion. Similarly, the discoid portions 122, 124 may include upper portions 136, 138 that are separated by a smaller distance than lower portions 140, 142. Furthermore, the discoid portions 122, 124 of the inner member 112 may have a larger radius than the discoid portions 116, 118 of the outer member 114. Thus, the overlying portions of the inner 112 and outer 114 members may exhibit greater clamping force than the non-overlying portions. Moreover, the inner 112 and outer 114 members could also include different properties (e.g., stiffness) to vary the clamping force. As described above, the proximal 125 and distal 127 ends of the device 110 may be secured with respective end clamps 129, and the lower portions 140, 142 may include respective openings 131 configured to receive the proximal and distal ends of the lower portions 140, 142 such that the ends of the discoid portions may be secured with the same end clamp.

It is understood that the configuration of the medical device 110 may be varied in order to treat different target sites and patients. For example, the medical device 110 may only include the inner 112 or outer 114 member, and each member may include one or more layers of material. FIG. 20 shows a variation of a medical device 150 having a varying width waist. In particular, FIG. 20 depicts a medical device 150 having a pair of full discoid portions 152, 154 that are coupled by a central portion 156. The discoid portions 152, 154 are separated by a non-uniform distance along axis C. More specifically, each discoid portion 152, 154 includes a respective upper portion 158, 160 and a lower portion 162, 164, wherein the upper portions are separated by a smaller distance measured along central axis C than the lower portions. Thus, the medical device 150 may be suitable for accommodating target sites having varying sizes. For instance, FIG. 20 shows that the medical device 150 may be employed to treat a PMVSD, wherein the upper portions 158, 160 overlie the membranous portion of the septum, while the lower portions 162, 164 overlie the muscular portion of the septum.

Embodiments of the present invention may provide several advantages. According to one embodiment, the medical devices may include an asymmetrical configuration that is adaptable for a variety of lumens to improve fixation and treatment of a target site. For example, the medical devices may be asymmetric in its material properties (e.g., stiffness) and/or geometry (e.g., cross section). In one embodiment, the medical device may include different properties for applying an asymmetric clamping force. Varying the clamping force may be beneficial for treating ventricular septal defects, which may reduce the incidence of heart block, abrading the left ventricle, or interfering with the aortic valve. Moreover, the medical device may be used to occlude, shunt, restrict flow in vessels, channels, lumens, cavities, or organs anywhere in the vasculature or body.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical device comprising:
a first tubular member that includes a first portion, a second portion, and a central portion disposed between said first portion and said second portion, wherein the first tubular member has a central axis extending between said first and second portions, wherein said central portion is disposed axially along the central axis, wherein each of said first portion and said second portion has a radius defined about the central axis that is larger than that of said central portion, and wherein said second portion has a partial discoid shape in a preset, relaxed configuration defined by a radial inversion of a portion of a discoid into itself along a plane perpendicular to the central axis.

2. The medical device of claim 1, wherein said first portion has a preset, relaxed configuration in which said first portion has a partial discoid shape defined by a radial inversion of a portion of a discoid into itself along a plane perpendicular to the central axis.

3. The medical device of claim 1, wherein said tubular member includes at least one layer of fabric.

4. The medical device of claim 3, wherein said at least one layer of fabric comprises a plurality of braided strands.

5. The medical device of claim 3, wherein said at least one layer of fabric comprises a shape memory alloy.

6. The medical device of claim 3, wherein said at least one layer of fabric is configured to facilitate thrombosis.

7. The medical device of claim 1, further comprising a second tubular member coupled to said first tubular member and including a first portion, a second portion, and a central portion disposed between said first and second portions of said second tubular member, wherein said first and second portions of said second tubular member have radii larger than that of said central portion of said second tubular portion.

8. The medical device of claim 7, wherein said first and second tubular members are coupled such that at least a portion of said second portion of said first tubular member is received by said first or said second portion of said second tubular member.

9. The medical device of claim 7, wherein said second portion of said second tubular member has a partial discoid shape in a preset, relaxed configuration defined by a radial inversion of a portion of a discoid into itself.

10. The medical device of claim 9, wherein said first and second tubular members are coupled such that said partial discoid shape portions of said second portions of said first and second tubular members are adjacently disposed such that said second portions of said first and second tubular members cooperate to define a substantially disk-shaped structure.

11. The medical device of claim 10, wherein said second portions of said first and second tubular members are half-disk shaped and are adjacently disposed such that said second portions of said first and second tubular members cooperate to define a substantially disk-shaped structure.

12. The medical device of claim 9, wherein said first and second tubular members are coupled such that at least a portion of said partial discoid shape portion of said second portion of said first tubular member receives at least a portion of said second portion of said second tubular member.

13. The medical device of claim 7, wherein said first and second tubular members are at least partially formed of respective materials having differing stiffness.

14. The medical device of claim 7, wherein said first and second tubular members include respective layers of metallic fabric having differing densities of braided strands.

15. The medical device of claim 7, wherein said first and second tubular members include respective first and second layers of metallic fabric, and wherein said first layer of metallic fabric includes strands of a diameter different than a diameter of strands of the second layer of metallic fabric.

16. The medical device of claim 1, wherein said first portion is disk shaped.

17. The medical device of claim 1, wherein said first and second portions are half-disk shaped.

18. The medical device of claim 1, wherein said first and second portions have a different stiffness.

19. The medical device of claim 1, wherein said first tubular member is configured to be positioned within a septum, and wherein said first and second portions are configured to provide an asymmetrical clamping force on the septum.

20. The medical device of claim 1, wherein said tubular member includes a single layer of fabric, and wherein said second portion has a partial discoid shape defined by a radial inversion of a portion of a discoid into itself such that the second portion includes a pair of overlapping layers of fabric.

21. The medical device of claim 1, wherein said second portion is a half-disk shape defined by a radial inversion of a disk shape into itself.

22. The medical device of claim 1, wherein the first tubular member has proximal and distal ends, and wherein the first tubular member is radially inverted along the entire length between the proximal and distal ends such that a portion of each of the first portion, the second portion, and the central portion is radially inverted within itself, wherein each of said first and said second portions is radially inverted within itself along a plane perpendicular to the central axis, and wherein said central portion is radially inverted within itself along a plane parallel to the central axis.

23. A medical device comprising:
a first tubular member comprises a first portion, a second portion, and a central portion disposed between said first portion and said second portion, wherein the first tubular member has a central axis extending between said first and second portions, and wherein said central portion is disposed axially along the central axis, wherein each of said first portion and said second portion has a radius defined about the central axis that is larger than that of said central portion, and wherein said second portion has a radially concave surface defined by a radial inversion into itself along a plane perpendicular to the central axis.

24. The medical device of claim 23, wherein at least a portion of the central portion has a radially concave surface defined by a radial inversion into itself along a plane parallel to the central axis.

* * * * *